United States Patent [19]

Ross-Petersen

[11] 4,065,461
[45] Dec. 27, 1977

[54] AMINO CONTAINING PYRIDYLOXY PROPANOLS

[75] Inventor: Karl Jakob Ross-Petersen, Farum, Denmark

[73] Assignee: Aktieselskabet Grindstedvaerket, Arhus N, Denmark

[21] Appl. No.: 713,166

[22] Filed: Aug. 10, 1976

[30] Foreign Application Priority Data

Aug. 12, 1975 United Kingdom ............... 33474/75

[51] Int. Cl.² .................. C07D 213/65; C07D 213/73
[52] U.S. Cl. ............................. 260/296 AE; 424/263
[58] Field of Search ................. 260/296 AE

[56] References Cited

U.S. PATENT DOCUMENTS

| | | | |
|---|---|---|---|
| 3,328,417 | 6/1967 | McLoughlin et al. | 260/307 |
| 3,535,328 | 10/1970 | Zielinski | 260/296 AE |
| 3,723,476 | 3/1973 | Nakanishi et al. | 260/296 AE X |

OTHER PUBLICATIONS

Kerwin et al., J. Am. Chem. Soc. vol. 73, pp. 4162 to 4168 (1951).

*Primary Examiner*—Henry R. Jiles
*Assistant Examiner*—R. W. Ramsuer
*Attorney, Agent, or Firm*—Lawrence Rosen; E. Janet Berry

[57] ABSTRACT

As new compounds having β-receptor blocking activity, isopropylamino-(pyridyloxy)-propanols with the general formula

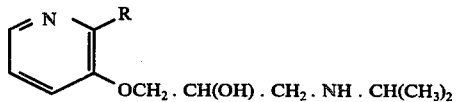

wherein R denotes hydrogen or amino. The compounds are prepared by reacting a corresponding 3-pyridinol with epichlorohydrin and the resulting product with isopropylamine.

3 Claims, No Drawings

AMINO CONTAINING PYRIDYLOXY PROPANOLS

BRIEF DESCRIPTION OF THE INVENTION

This invention relates to new compounds of β-adrenergic blocking activity.

The new compounds of the invention are represented by the following formula

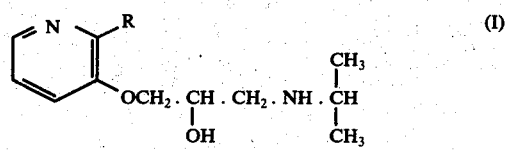

wherein R represents hydrogen or an amino group, or are acid addition salts thereof.

BACKGROUND OF THE INVENTION

During later years, compounds having blocking activity on the β-adrenergic receptors having gained increasing importance, i.a. as tranquilizers and medicines against various heart and vascular diseases such as heart arrythmias, and angina pectoris. It has been established that there exist two types of β-receptors, for convenience called $β_1$-receptors and $β_2$-receptors. $β_1$-receptors are predominant, i.a., in the heart and $β_2$-receptors predominant, i.a., in the bronchia and blood vessels. It has also been established that some compounds act more or less indiscriminately on both types of β-receptors; an outstanding example of this type of compounds is propranolol, i.e., 1-(isopropylamino)-3-(1-naphthyloxy)-2-propanol. Other compounds have a blocking activity predominantly on either the $β_1$-receptors or the $β_2$-receptors. If a compound has blocking activity on the $β_1$-receptors and not on the $β_2$-receptors it can be considered promising as a drug for the treatment of, i.a., hypertension and is furthermore likely to be tolerated by asthma patients. An example of a compound having substantial blocking activity on the $β_1$-receptors and not on the $β_2$-receptors is practolol which suffers, however, from the disadvantage that it has some intrinsic effect and side effects. Great effort have been made to find compounds having a high specificity for blocking $β_1$-receptors and being free from side effects and intrinic effects on the β-receptors and also requiring small dosages, i.e. being highly active.

A rather recent development in the field of compounds having β-adrenergic blocking activity is represented by Belgian Pat. No. 811,274 to Ciba-Geigy AG. It claims a large number of compounds including compounds having the general formula

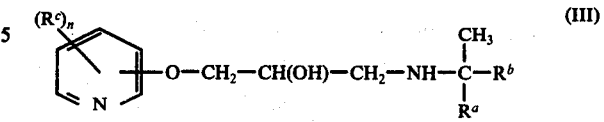

wherein Het (amongst other possibilities) is a substituted pyridyl radical, $R^a$ a hydrogen atom or a methyl group, and $R^b$ (amongst other possibilities) a lower alkyl group. Accordingly, a compound of formula I above wherein R is hydrogen, is not claimed. A compound of formula I wherein R is amino is claimed but not disclosed and probably not contemplated. The reason for this assumption is that a subclaim claims pyridyl derivatives of the formula

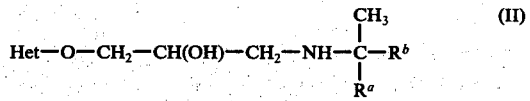

$R^a$ and $R^b$ have, i.a., the above meanings, n is 1, 2, or 3 and wherein $R^c$, amongst other meanings, may be alkyleneamino, thiaalkyleneamino, hydroxyalkyleneamino, alkylamino, dialkylamino, acylamino, but not unsubstituted amino; of course, no compound with such an unsubstituted amino group is disclosed.

DETAILED DESCRIPTION OF THE INVENTION

It is an object of the present invention to provide novel compounds having β-adrenergic blocking activity such that the blocking activity has a high degree of specificity on the $β_1$-receptors. It is a further object of the invention to provide such compounds having a low degree of intrinsic activity and a low degree of side effects. Furthermore it is an object of the invention to provide such compounds having low toxicity. A still further object of the invention is to provide a process for preparing the compounds of the general formula I.

The compounds of the invention have been examined for β-blocking activity and especially for the specificity for $β_1$ and $β_2$-receptors and compared in these respects with propranolol, practolol and some very closely related compounds representative of the abovementioned Belgian patent. The same compounds have furthermore been examined for toxicity.

The examinations thus comprise selective effect against isoprenaline-induced changes in heart rate, which are presumed to be elicited by stimulation of $β_1$-receptors; and against the reduction in tone in the peripheral vasculature induced by the said agonist is presumed to be due to stimulation of $β_2$-receptors.

The test animals were adult cats of either sex. Prior to the examination, the cats were anaesthetized by injection of pentobarbitone sodium (45 mg/kg), and during the experiment, each cat was dosed intraveneously as required with small doses of pentobarbitone sodium in order to obtain a steady systolic blood pressure of about 75 mm Hg.

The heart rate was derived electronically from the blood pressure in the right carotid artery, and the reduction in tone in the peripheral vasculature was determined by recording changes in hind quarter vascular resistance.

Each cat was dosed repeatedly at 15 minutes' intervals throughout the experiment with 1 μg isoprenaline as the hydrochloride, the dose of this and the other standard drugs being stated in terms of the base. When constant responses of both heart rate and hind quarter perfusion pressure were obtained, a dose of 4 μg/kg of one of the test compounds was administered intraveneously 2 minutes before the isoprenaline dose. This initial dose of the test compound was administered again 15 minutes later. Thereafter, the test compound was administered at 15 minutes' intervals, each successive dose being twice the preceeding dose, the injection always being given two minutes prior to the next isoprenaline dose. The dose was increased until the isoprenaline-induced change in heart rate or hind quarter perfusion pressure or both were greatly reduced. In this way, cumulative dose-response curves for the effects of each test compound could be calculated and approximately $ED_{50}$ values obtained.

The approximate $ED_{50}$ values for $\beta_1$ and $\beta_2$-adrenoreceptor blockade and the ratio between these two activities are presented in Table I.

In this, compounds are identified as follows:

Compound 1: compound of general formula I, R=H
Compound 2: compound of general formula I, R=NH$_2$
Compound 3: practolol
Compound 4: propranolol
Compound 5: compound of formula IV, $R^1$=CH$_3$, $R^2$=H
Compound 6: compound of formula IV, $R^1$=H, $R^2$=Cl Formula IV:

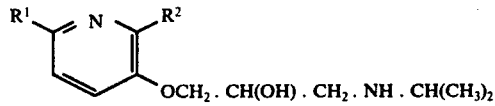

Table I

| Compound No. | Approximate ED$_{50}$ value ($\mu$g/kg) for | | Ratio $\frac{ED_{50}\beta_2}{ED_{50}\beta_1}$ |
| --- | --- | --- | --- |
| | $\beta_2$-receptor blockade | $\beta_1$-receptor blockade | |
| 1 | 1,450 | 7 | 207.1 |
| 2 | 3,500 | 80 | 43.8 |
| 3 | 10,400 | 360 | 28.9 |
| 4 | 32 | 70 | 0.54 |
| 5 | > 4,096 | 700 | > 5.8 |
| 6 | 1,350 | 30 | 45.0 |

Toxicity tests were carried out on mice. By oral administration, it was found that a dosage of up to 1000 mg/kg of the compounds of formula I did not kill any of the mice whereas propranolol at this dosage killed 2 of 5 male and 1 of 5 female mice. The oral LD$_{50}$ was not determined.

The toxicity at intravenous administration was also tested and the LD$_{50}$ determined. The results are shown in Tabel II.

Table II

| Treatment | Sex | LD$_{50}$ (mg/kg) | 95% confidence limits |
| --- | --- | --- | --- |
| 1 | ♂ | 261.1 | 198.1 – 344.1 |
|   | ♀ | 285.2 | 212.0 – 383.8 |
| 2 | ♂ | 203.4 | 168.6 – 257.7 |
|   | ♀ | 192.0 | 134.7 – 273.9 |
| 3 | ♂ | 41.6 | 31.3 – 55.2 |
|   | ♀ | 31.6 | 22.9 – 43.4 |
| 4 | ♂ | 165.0 | 125.3 – 217.3 |
|   | ♀ | 151.3 | 114.9 – 199.3 |
| 5 | ♂ | 285.2 | 212.0 – 383.8 |
|   | ♀ | 239.4 | 181.7 – 315.6 |
| 6 | ♂ | 165.0 | 125.3 – 217.3 |
|   | ♀ | 180.2 | 134.0 – 242.2 |

The data in Table I indicate that of the reference standards, propranolol is highly active but does not antagonize either $\beta_1$ og $\beta_2$-receptors selectively. Although much less active than propranolol, practolol shows approximately thirty times more selectivity against the $\beta_1$-receptors than against $\beta_2$-receptors.

The compounds of the invention have a potency approximately equal to (R=NH$_2$) or greater than (R=H) propranolol as antagonists of the $\beta_1$-receptors and are therefore much more active in this respect than practolol, and both compounds of the invention show a higher ratio of specificity in favour of $\beta_1$-receptor blockade than does either of the reference standards.

The compounds of the invention also compare favourable with the compounds of formula IV tested. Especially compound No. 1, i.e. the compound of formula I wherein R is a hydrogen atom, has outstanding selectivity as $\beta_1$-adrenoblocking agent and being at the same time extremely active as expressed by a very low ED$_{50}$ in this respect. From Table II it is learned that this compound also has a low toxicity, expressed by the LD$_{50}$ being better than all of the compounds tested for comparison except compound No. 5 which on the other hand is not very active and has a rather low degree of selectivity. The other compound of the invention (R = amino) also has a high degree of selectivity, being in this respect equal to the best of the compounds tested for comparison (No. 6), and being somewhat less toxic.

The results indicate that the compounds of the invention will be suitable as drugs for the treatment of heart and vascular diseases such as heart arrhythmia, angina pectoris, and arterial hypertension, either alone or in combination with other compounds having similar effect or — as far as treatment for hypertension is concerned — act as diuretics. For therapeutic purposes, the compounds of the invention, either as such or in form of their acid addition salts, are administered parenterally or preferably orally in a dose ranging (for adult persons) from 5 mg to 500 mg per day, the exact dose depending on the age, weight and condition of the patient and on the possible simultaneous treatment with other drugs. The compounds may be worked up for pharmacological purposes according to standard pharmaceutical practice whereby conventional carries and/or excipients are incorporated. The compositions may have the form of tablets, capsules, syrups or other liquid preparations for oral administration and are preferably tablets with or without a coating. Each tablet may contain from 2 mg to 500 mg of the active component. The compositions may also be for parenteral administration such as compositions (solutions or suspensions) for intravenous injection.

PREPARATION OF THE COMPOUNDS

The best way of preparing the compounds known at present according to the invention consists in (a) reacting a 3-pyridinol having the general formula

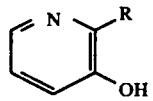 V wherein R has the meaning defined in connection with formula I, with epichlorohydrin and (b) reacting the resulting product with isopropylamine. The 3-pyridinol used as starting material is conveniently used in the form of a salt thereof, preferably the sodium salt. The reaction of step (a) is experdiently carried out in a solvent, preferably dimethylsulfoxide. The reaction of step (b) is also preferably carried out in a solvent. As solvent may be used an excess of the isopropylamine but preferably an inert solvent or co-solvent is also present. As examples of suitable solvents may be mentioned lower alkanols such as methanol.

The reaction scheme is, R being as defined:

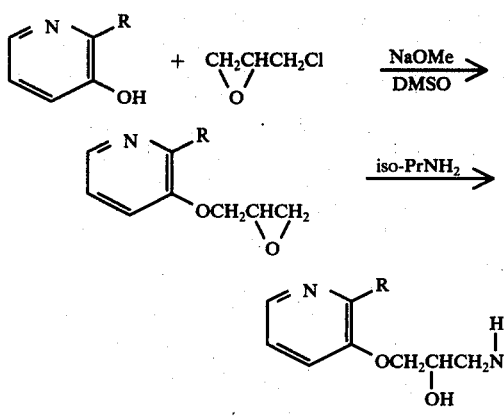

The compound of formula I may be used as such or may be converted into an acid addition salt with a non-toxic acid which may be inorganic such as hydrochloric, hydrobromic, sulfuric, nitric or phosphoric acid; or organic such as p-toluenesulfonic, citric, lactic, or ascorbic acid.

However, some other processes for preparing the compounds are also contemplated. Thus, the reaction of a compound of general formula V above with a compound of the general formula

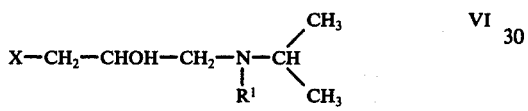

wherein X is a reactive, esterified hydroxy group and $R^1$ is a group which can be readily cleaved in a manner known per se.

A reactive, esterified hydroxy group is a hydroxy group esterified with a strong inorganic or organic acid, for instance with a hydrogen halide such as hydrogen chloride or bromide, or with sulphuric acid; an example of a useful strong organic acid is a strong organic sulphonic acid such as methane sulphonic acid or 4-toluene sulphonic acid.

A group which can be readily cleaved in a manner known per se is one of the numerous amino-protecting groups known, i.e. a group that can readily be split off by hydrolysis or hydrogenolysis and replaced by a hydrogen atom. Groups that can be split off by hydrolysis especially are acyl groups such as lower alkanoyl groups, arylloweralkanoyl groups such as the benzoyl group or alkylor arylsulphonyl groups such as methanesulphonyl or p-toluenesulphonyl group. Groups that can be split off by hydrogenolysis usually are groups that can be cleaved by conventional hydrogenolysis by the aid of hydrogen and a metal catalyst. Examples of such groups are α-aralkyl groups such as the benzyl group. A preferred group $R^1$ is a benzyl group.

Thus, one can react 3-pyridinol (or 2-amino-3-pyridinol) with 1-(benzylisopropylamino)-3-chloro-2-propanol under the same conditions as described above for the reaction of compound V with epichlorohydrin. Subsequently, the benzyl group is removed, e.g. by catalytic reduction with hydrogen and a suitable catalyst, e.g. 5% palladium on carbon at atmospheric pressure and in a solvent. The solvent may be a lower alkanol such as methanol.

A compound of the general formula I wherein R is an amino group can also be prepared from a corresponding compound wherein R is a nitro group or an acylamino group, by reduction or hydrolysis, respectively, in a manner well known to chemists. Starting materials for these reactions have the general formulae

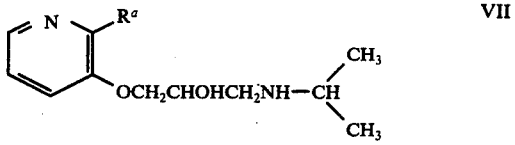

and

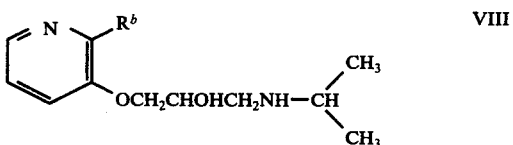

wherein $R^a$ denotes a nitro group and $R^b$ an acylamino group. These starting materials can be prepared from the corresponding 2-pyridinols

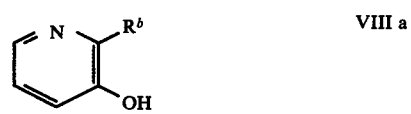

wherein $R^a$ and $R^b$ have the meanings stated, by reaction with epichlorohydrin and reaction of the product with isopropylamine; this is a reaction analogous with the first described reaction for forming compounds I.

Furthermore, it is possible to react a compound having the general formula

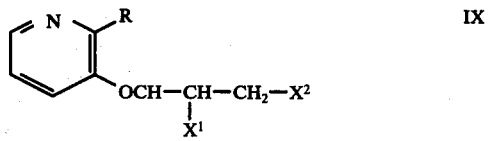

with a compound having the general formula

in which formulae R has the above meaning, and wherein $X^1$ is a hydroxy group, or wherein $X^1$ and $X^2$ together are an epoxy group if $X^3$ is an amino group, one of groups $X^2$ and $X^3$ being an amino group and the other a reactive, esterified hydroxy group. The reactive, esterified hydroxy group is a group as explained above in connection for formula VI. The reaction is carried out in conventional manner, preferably in the presence of an alkaline condensation agent. Suitable alkaline condensation agents are for instance alkali metal hydroxides such as sodium or potassium hydroxide, or alkali metal alcoholates such as sodium methylate or ethylate.

A compound of the general formula I can also be prepared by the reduction of a Schiff's base having the general formula

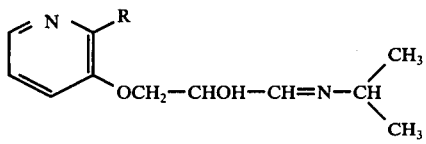

XI or

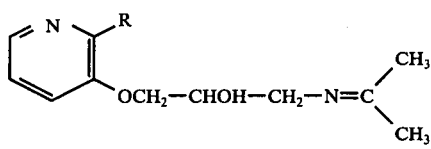

XII in conventional manner, e.g. by reduction with hydrogen in the presence of a hydrogenation catalyst, for instance a noble metal catalyst such as palladium on carbon.

A compound of the general formula I wherein R is a hydrogen atom can be prepared from the amino compound of formula I by protecting the amino group in the 3-side chain, deaminating in position 2 and removing the protective group, i.e. by deamination a compound of the general formula

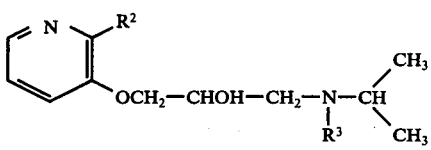

XIII wherein $R^2$ is an amino group and $R^3$ a protective group (for instance one of those discussed above for $R^1$) which can be readily cleaved, after which $R^3$ is removed.

When the desired compound of formula I has been prepared in its racemic form, it can be split in conventional manner into the pure optically active antipodes. If the compound has been obtained in the free base form, it may be converted into a pharmaceutcially acceptable acid addition salt and if it has been obtained as an acid addition salt, the free base may be liberated therefrom, or an acid addition salt formed may be converted into another, pharmaceutically acceptable acid addition salt.

Some Examples serve at illustrating the process of the invention.

EXAMPLE 1

1-Isopropylamino-3-(3-pyridyloxy)-2-propanol

A solution of sodium (2.30 g, 0.100 mole) in methanol (40 ml) was added to a solution of 3-pyridinol (9.50 g, 0,100 mole) in dimethylsulfoxide (100 ml), and the methanol was removed by distillation (100° C, 10 mm Hg). To the resulting solution of the sodium salt of 3-pyridinol at 25° C was added epichlorohydrin (10.2 g, 0,110 mole). The mixture was kept under stirring at 25° C for 4 hours. The resulting black suspension was diluted with ice-water (500 ml) and extracted with chloroform (100 + 75 + 50 + 25 ml). The combined chloroform extracts were washed with water (50 ml), dried over sodium sulfate, and evaporated on a water bath (50° C, 10 mm Hg).

The resulting tea-coloured oil (4.75 g) was dissolved in a mixture of methanol (25 ml) and isopropylamine (15 ml) and heated to 100° C in a rocker-type autoclave overnight. After cooling, the solvent was removed on a water bath (60° C, 10 mm Hg), and the residual tea-coloured oil (7.60 g) was heated under reflux with decolourizing carbon (1 g) in toluene (50 ml) for 10 minutes. The carbon was removed by filtration of the hot mixture, and the filter cake was washed with hot toluene (12 + 12 ml). Cooling under stirring, filtration of the formed crystals, washing with toluene (10 ml), and drying (50° C, 10 mm Hg) gave the title compound as light tea-coloured crystals, melting at 84°-87° C.

For analysis, a sample was purified by crystallization once from ethyl acetate and once from toluene, the m.p. raising to 89°-90° C.

Calculated for $C_{11}H_{18}N_2O_2$(210.3): C, 62.8; H, 8.6; N, 13.3. Found: C, 62.4; H, 8.6; N, 13.3.

EXAMPLE 2

1-Isopropylamino-3-[(2-amino-3-pyridyl)oxy]-2-propanol

A solution of sodium (1.15 g, 0,0500 mole) in methanol (20 ml) was added to a solution of 2-amino-3-pyridinol (5.50 g, 0.0500 mole) in dimethylsulfoxide (50 ml), and the methanol was removed by distillation (100° C, 10 mm Hg). To the resulting suspension of the sodium salt of 2-amino-3-pyridinol at 25° C was added epichlorohydrin (5.10 g, 0,055 mole). The dark violet mixture was stirred at 25° C for 4 hours. The resulting dark tea-coloured solution was diluted with ice-water (250 ml) and extracted with chloroform (50 + 50 + 50 + 25 ml). The combined chloroform extracts were washed with water (25 ml), dried over sodium sulfate, and the chloroform was evaporated on a water bath (50° C, 10 mm Hg).

The resulting light tea-coloured oil (4.20 g) was dissolved in a mixture of methanol (20 ml) and isopropylamine (15 ml) and heated under reflux for 3 hours. The solvent was evaporated on a water bath (60° C, 10 mm Hg). The residual light tea-coloured oil (4.64 g) was dissolved in toluene (25 ml) and estracted with 1N hydrochloric acid (15 + 10 ml) and water (10 ml). To the combined extracts was added 1N sodium hydroxide (25 ml), and the mixture was extracted with chloroform (15 + 10 + 10 ml). The combined chloroform extracts were washed with water (10 ml), and the chloroform was evaporated on a water bath (60° C, 10 mm Hg) giving 4.00 g of the title product, melting at 110° C (Kofler hot stage). 4.00 g of the product was crystallized from ethyl acetate (10 ml.) Filtration, washing with ethyl acetate (3 ml), and drying (50° C, 10 mm Hg) gave white crystals, melting at 112°-113° C.

For analysis 1.75 g were crystallized from ethyl acetate (10 ml) giving 1.50 g of white crystals with m.p. 113°-114° C.

Calculated for $C_{11}H_{19}N_3O_2$(255.3): C, 58.6; H, 8.5; N, 18.7. Found: C, 58.4; H, 8.4; N, 18.7.

EXAMPLE 3

1-Isopropylamino-3-(3-pyridyloxy)-2-propanol

A solution of sodium (1.15 g, 0.0500 mole) in methanol (20 ml) was added to a solution of 3-hydroxypyridine (4.75 g, 0,0500 mole) in dimethyl sulfoxide (50 ml). The methanol was removed by distillation from a water bath (80° C, 100 mm Hg). To the resulting solution of the sodium salt of 3-hydroxypyridine of 25° C was added 1-(benzylisopropylamino)-3-chloro-2-propanol (12.1 g, 0,0500 mole). The brown suspension was stirred at 55° C for 24 h. The black solution was diluted with ice-water (250 ml) and extracted with chloroform (100 + 50 + 25 ml). The combined chloroform extracts were washed with water (25 ml), N sodium hydroxide (25 + 25 ml), and again with water (25 ml). The extracts were dried over magnesium sulfate and evaporated to dryness from a water bath (60° C, 12 mm Hg) to give 6.7 g of a red oil. Crystallization from 2-butanone (25 ml) gave 1.8 g of a betaine with the formula

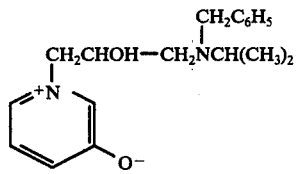

m.p. 142°–143° C, correct C, H, N analyses. From the mother liquor was obtained 3.4 g of a red oil which was triturated with petroleum ether (25 + 25 ml). The combined petroleum ether extracts were dried over magnesium sulfate and evaporated to give 2.5 g of a yellow oil. 1.1 g of this oil was dissolved in ethanol (7 ml), and palladium on carbon (5%, 0.1 g) was added. The mixture was kept under 1 atm of hydrogen at 50° C with stirring overnight. 140 ml (0.0058 mole) of hydrogen was hereby absorbed. The catalyst was removed by filtration and washed with ethanol (5 ml). The filtrate was evaporated from a water bath (60° C, 12 mm Hg), and the resulting oil was crystallized from ethyl acetate to give the title compound, m.p. 85°–88° C Calculated for $C_{11}H_{18}N_2O_2$(210.3): C, 62.8; H, 8.6; N, 13.3. Found: C, 62.8; H, 8.8; N, 12.8.

I claim:

1. A compound selected from the group consisting of

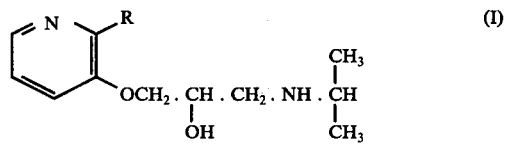

wherein R denotes a hydrogen atom or an amino group, and acid addition salts thereof.

2. A compound selected from the group consisting of 1-isopropylamino-3-(3-pyridyloxy)-2-propanol, and an acid additional salt thereof.

3. A compound selected from the group consisting of 1-isopropylamino-3-2-propanol, and its acid addition salts.

* * * * *